(12) United States Patent
Oh

(10) Patent No.: US 9,788,805 B2
(45) Date of Patent: Oct. 17, 2017

(54) DENTAL RAIDOGRAPHY DEVICE

(71) Applicant: Joon Ho Oh, Gwangju (KR)

(72) Inventor: Joon Ho Oh, Gwangju (KR)

(73) Assignee: RHT CO., LTD., Jeollanam-Do (KR)

( * ) Notice: Subject to any disclaimer, the term of this patent is extended or adjusted under 35 U.S.C. 154(b) by 0 days.

(21) Appl. No.: 14/894,333

(22) PCT Filed: Sep. 4, 2014

(86) PCT No.: PCT/KR2014/008297
§ 371 (c)(1),
(2) Date: Nov. 25, 2015

(87) PCT Pub. No.: WO2015/170804
PCT Pub. Date: Nov. 12, 2015

(65) Prior Publication Data
US 2017/0049409 A1   Feb. 23, 2017

(30) Foreign Application Priority Data

May 9, 2014   (KR) .................. 10-2014-0055916

(51) Int. Cl.
*A61B 6/14*   (2006.01)
*A61B 6/00*   (2006.01)
*H05G 1/10*   (2006.01)

(52) U.S. Cl.
CPC .............. *A61B 6/14* (2013.01); *A61B 6/461* (2013.01); *H05G 1/10* (2013.01); *A61B 6/40* (2013.01); *A61B 6/56* (2013.01)

(58) Field of Classification Search
CPC . A61B 6/56; A61B 2560/0214; A61B 6/4405; H01J 35/06; H05G 1/10; H05G 1/12; H05G 1/32; H05G 1/58; H05G 1/08; H05G 1/70
See application file for complete search history.

(56) References Cited

U.S. PATENT DOCUMENTS

2006/0098778 A1* 5/2006 Oettinger ................ H05G 1/06
378/101

FOREIGN PATENT DOCUMENTS

| KR | 10-2006-0068624 A | 6/2006 |
| KR | 10-2009-0053568 A | 5/2009 |
| KR | 20-0467938 Y1 | 7/2013 |
| KR | 10-2014-0039419 A | 4/2014 |

* cited by examiner

*Primary Examiner* — Hoon Song
(74) *Attorney, Agent, or Firm* — John K. Park; Park Law Firm

(57) ABSTRACT

The present invention relates to a dental radiography device capable of: reducing the amount of radiation exposure and the amount of battery consumption by reducing radiation exposure time by using a high switching frequency of 100 kHz or greater; preventing occurrence of operation errors caused by a momentary high voltage, etc. while using the high switching frequency; and easily setting X-ray irradiation time according to the type of teeth. Thus, the dental radiography device is safe, accurate and easy to use, and can have a small size and light weight.

7 Claims, 12 Drawing Sheets

[FIG. 1]
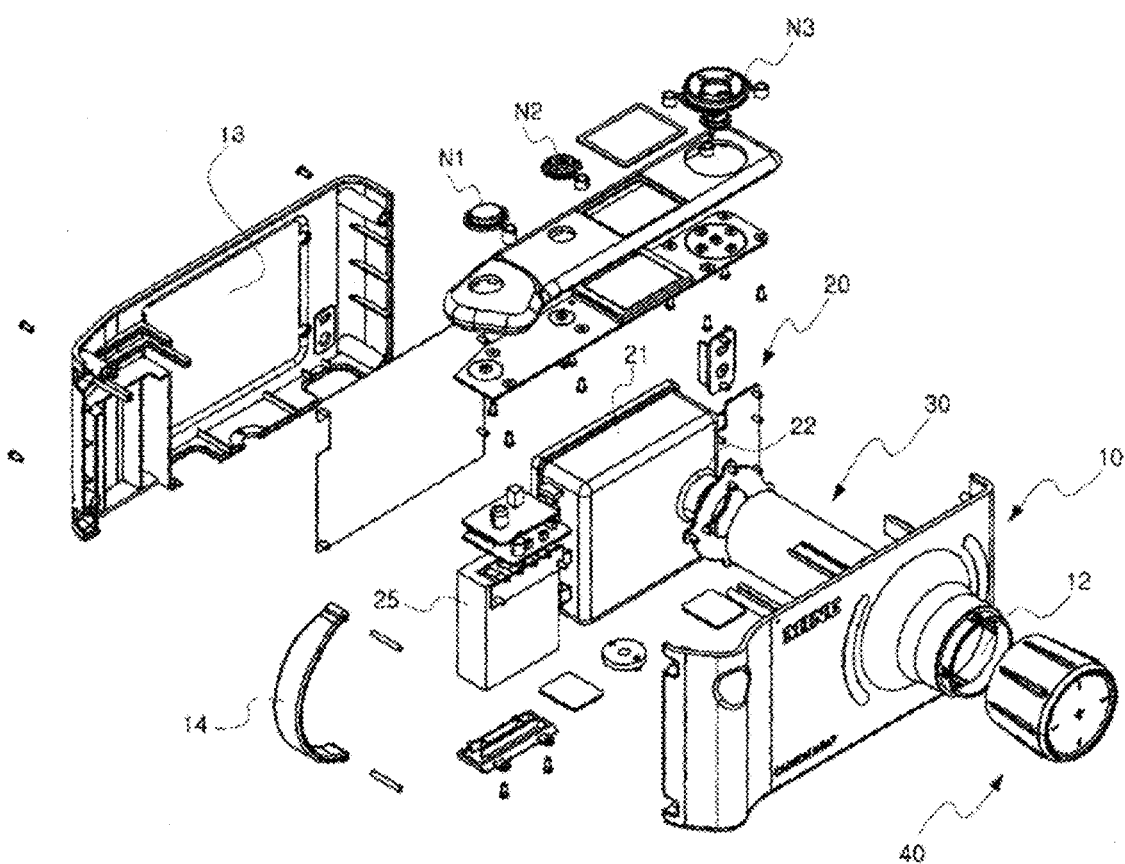

[FIG. 2]
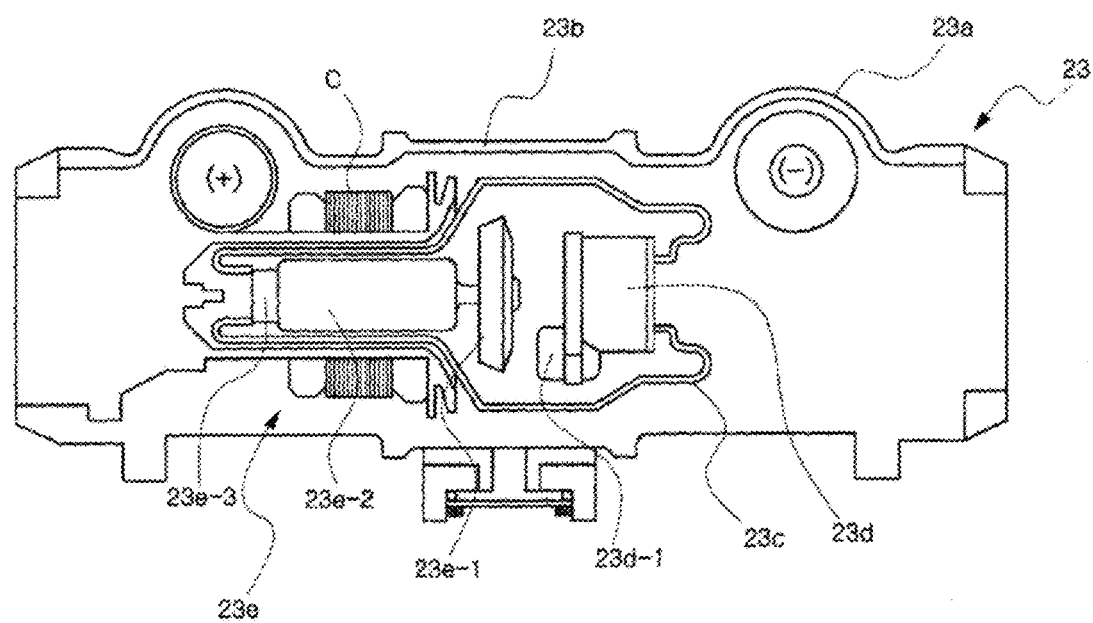

[FIG. 3]
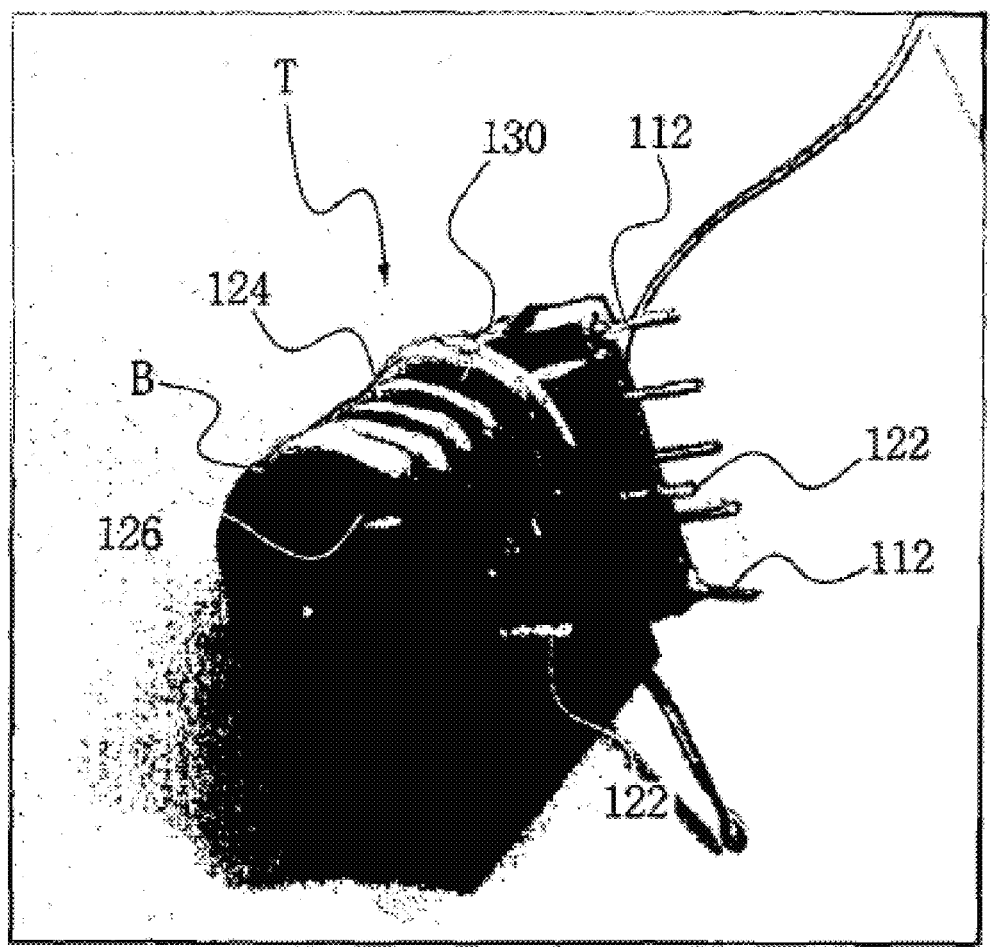

[FIG. 4]
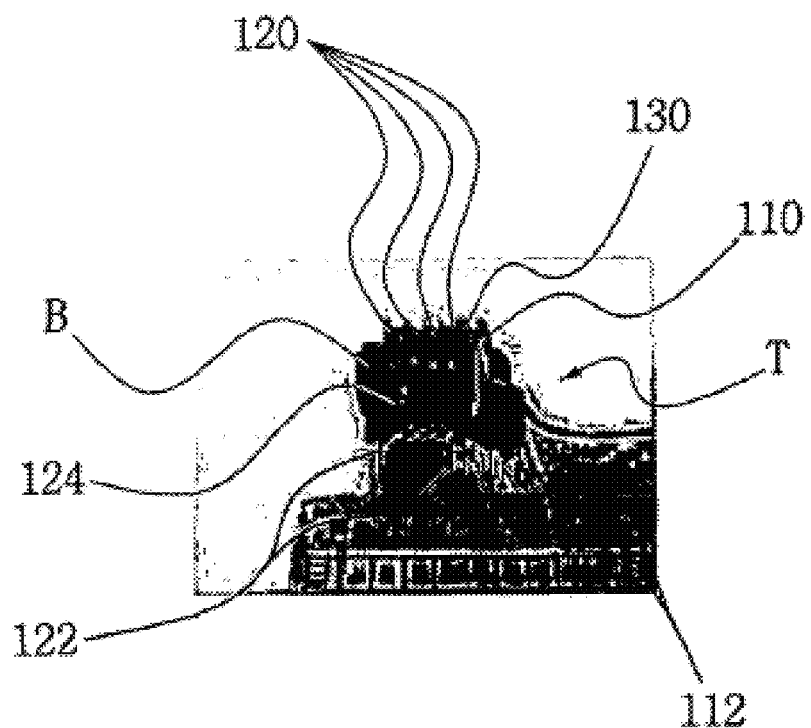

[FIG. 5]
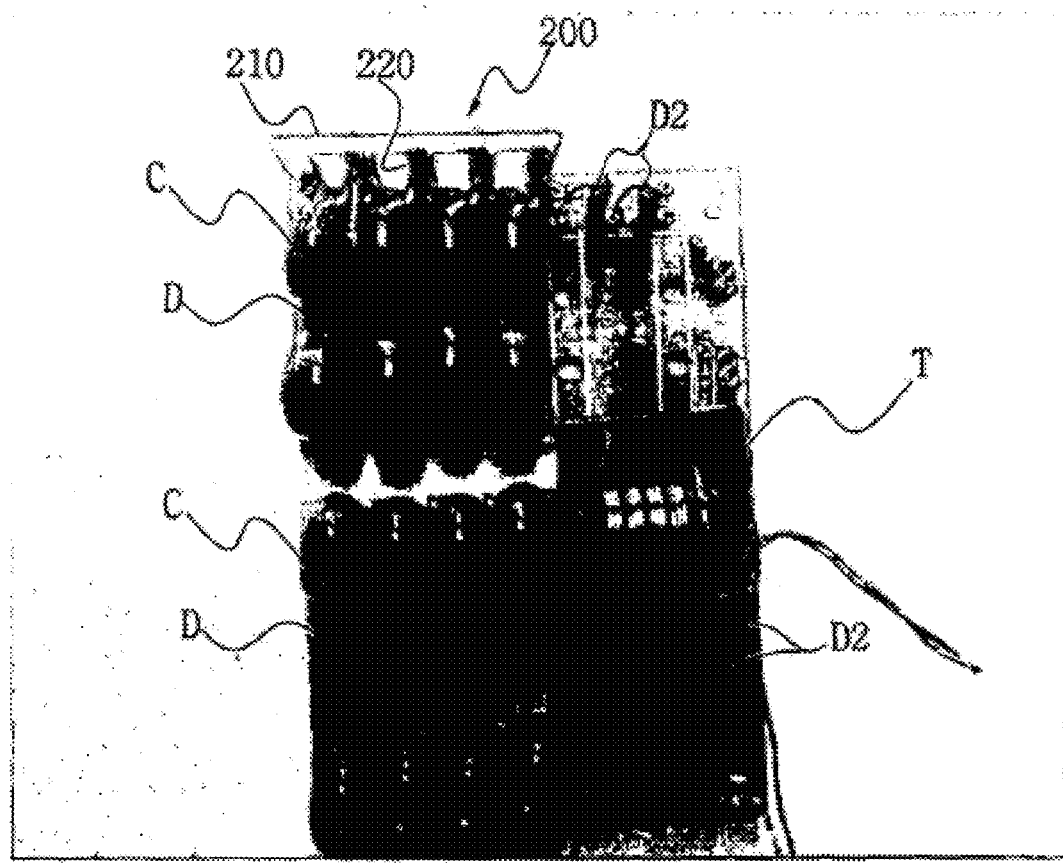

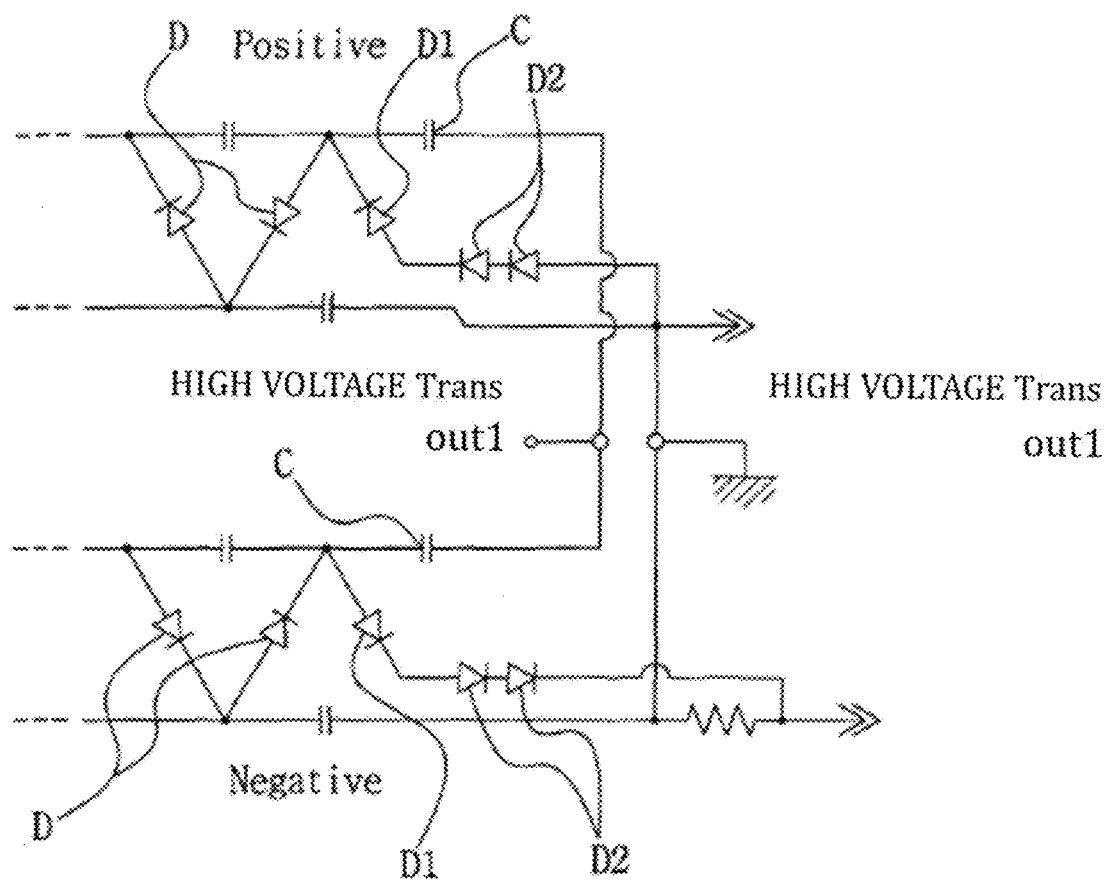
[FIG. 6]

[FIG. 7]
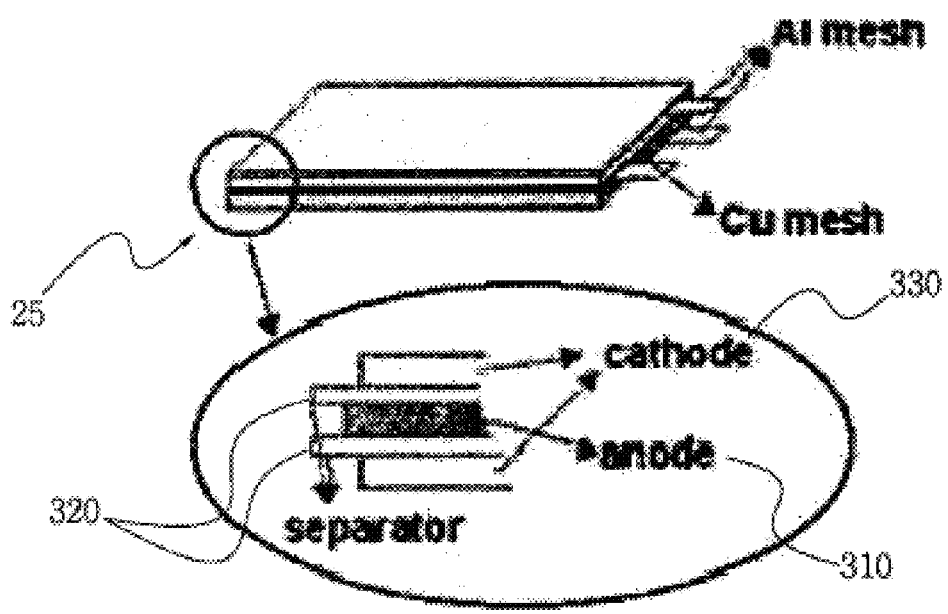

[FIG. 8]
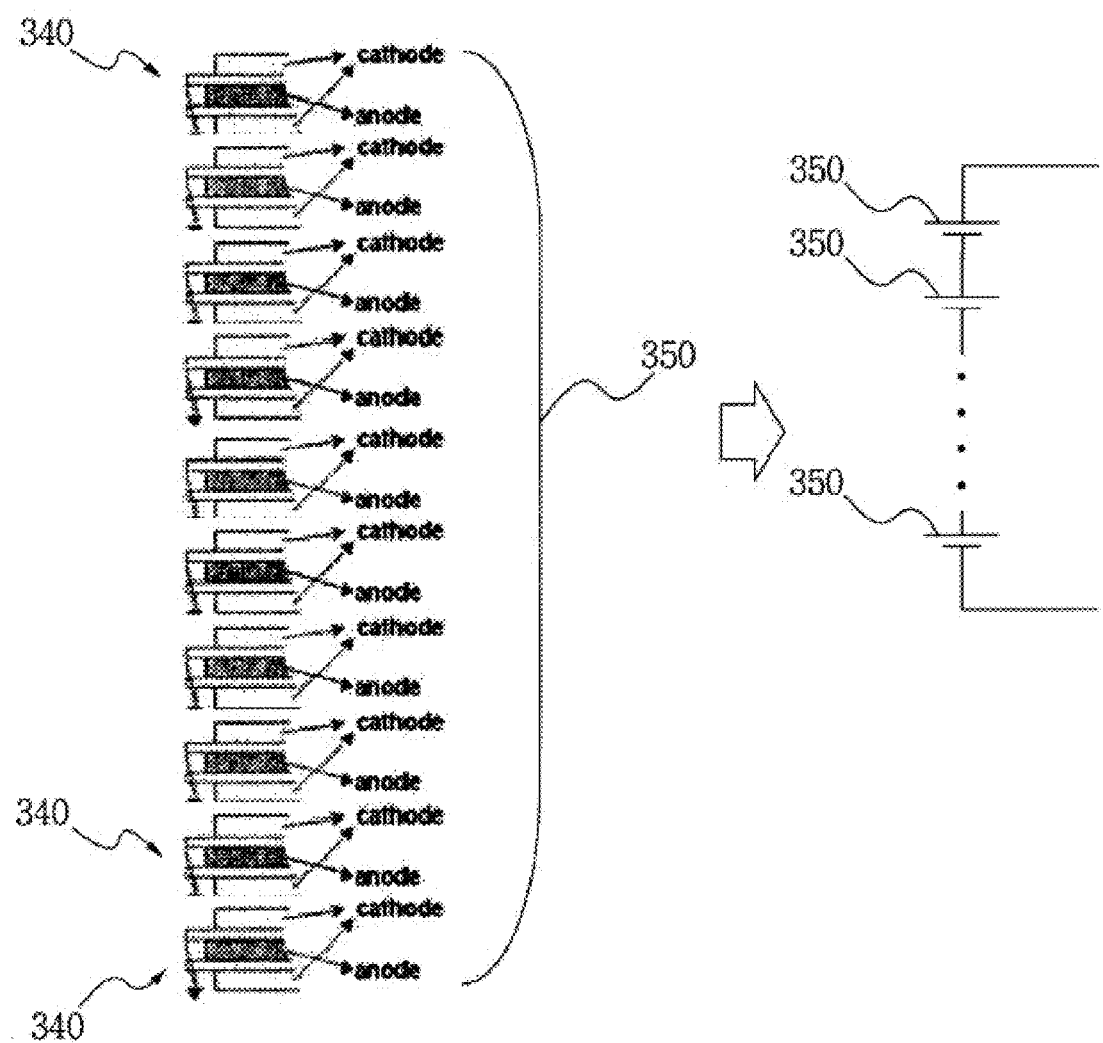

[FIG. 9]
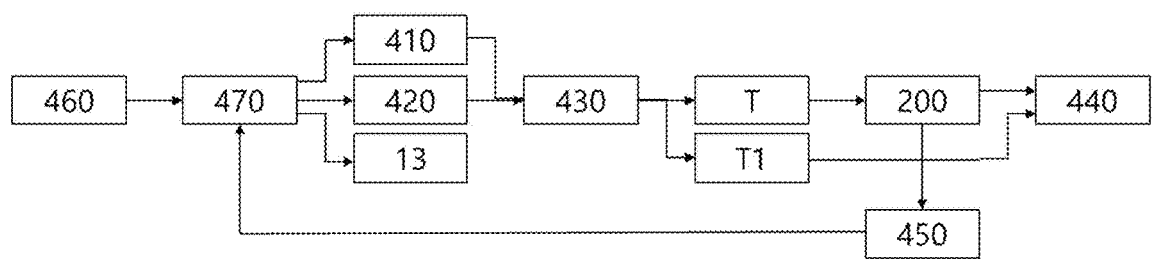
460: INPUT UNIT
410: TUBE VOLTAGE GENERATOR
13: DISPLAY UNIT
T: HIGH-VOLTAGE TRANSFORMER
200: HIGH-VOLTAGE MULTIPLYING CIRCUIT
450: DETECTING/CHECKING UNIT
470: CONTROL UNIT
420: TUBE CURRENT GENERATOR
430: SWITCHING UNIT
T1: FILAMENT TRANSFORMER
440: X-RAY TUBE

[FIG. 10]
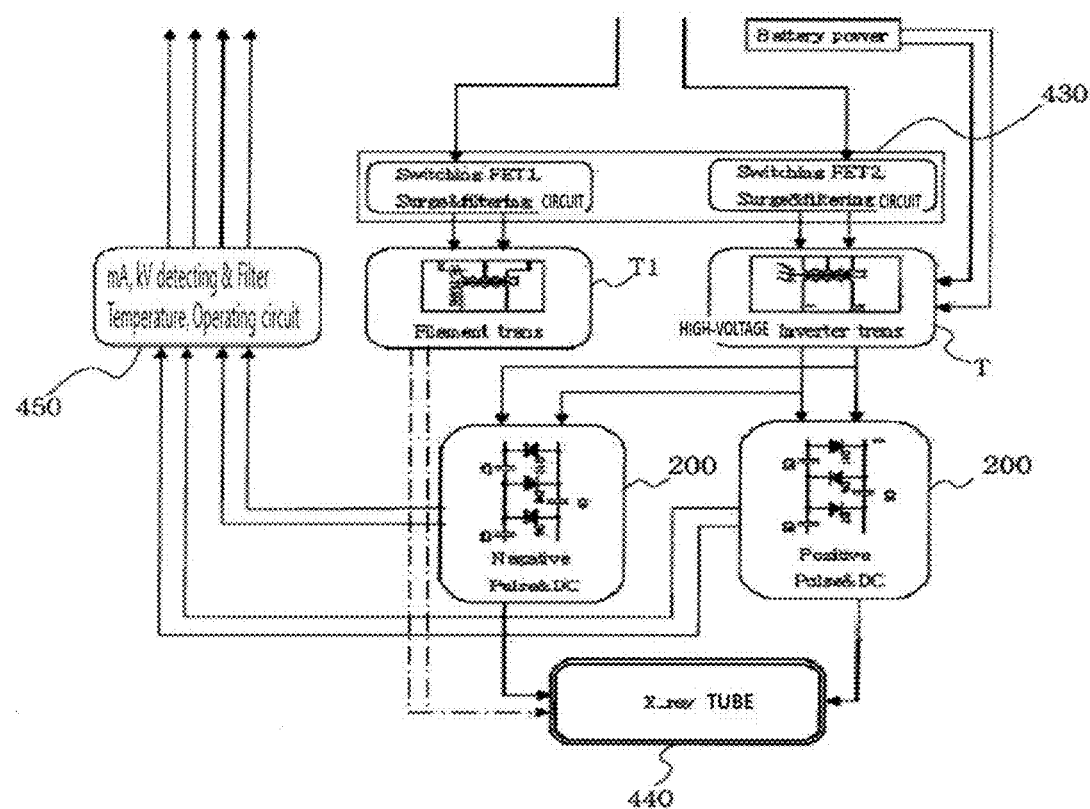

[FIG. 11]
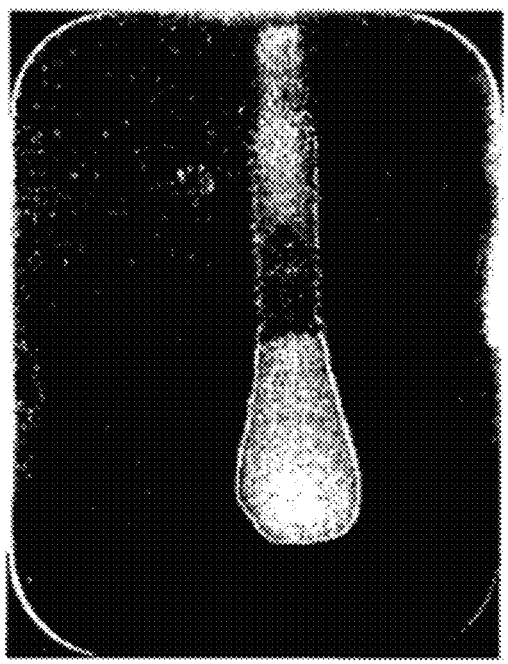 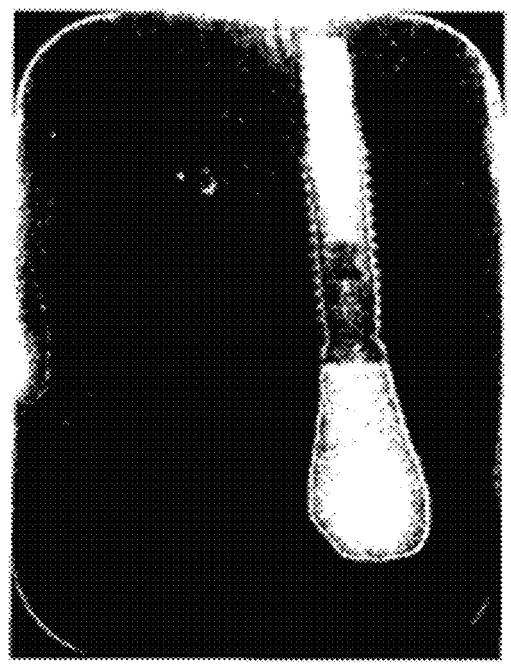
<RELATED ART>　　　　<INVENTION>

[FIG. 12]
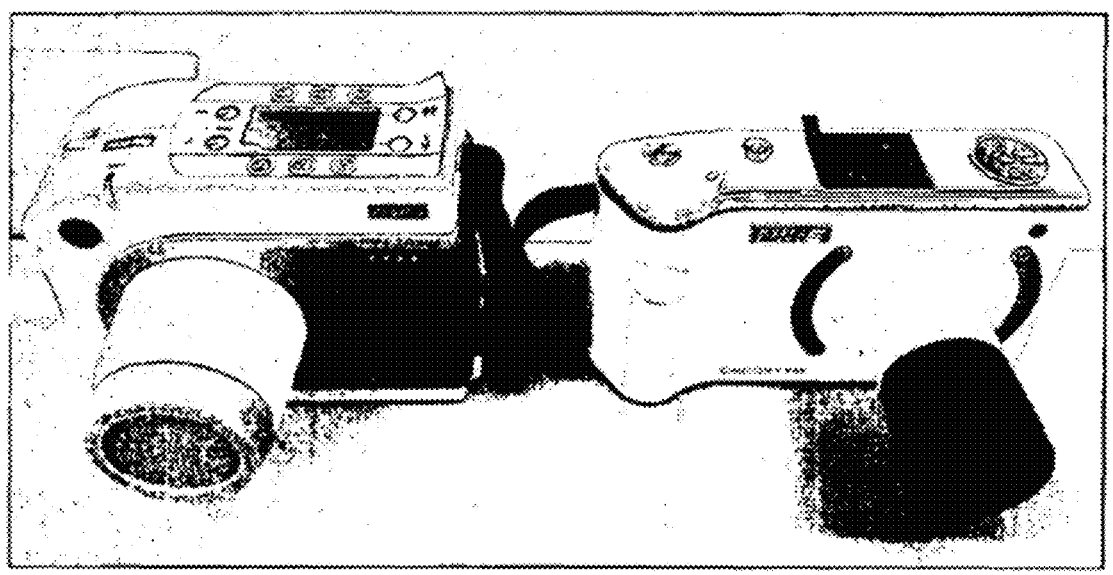
<RELATED ART>　　　　　<INVENTION>

DENTAL RAIDOGRAPHY DEVICE

TECHNICAL FIELD

The present invention relates to a dental radiography device and, more particularly, to a dental radiography device that can reduce an exposure dose and battery consumption by reducing an exposure time by using a high switching frequency of 100 kHz or more, that prevents malfunction due to sudden high voltage, that can easily set an X-ray radiation time in accordance with teeth, and that can be reduced in size and weight and can be used safely, accurately, and conveniently.

BACKGROUND ART

In general, a medical radiography device, which radiates X-rays to a human body and detects a difference in energy intensity distribution of the X-rays, falls into an analog type and a digital type.

The analog type, which uses an intensifying screen (fluorescent plate) and a silver halide film, makes a latent image on the silver halide film using light from the intensifying screen and then obtains a visual image by chemically processing the silver halide film. In the process of developing, costs are continuously generated, the film needs to be carefully managed, and waste water deteriorates the environment of a hospital.

On the other hand, the digital type, which uses a 2D sensor as a detector responding to X-rays, obtains a minute electrical signal generated by the sensor through a 2D matrix, converts an amplified signal into a digital value using an amplifying circuit that amplifies the minute signal, and an analog/digital converter makes an image data from the digital value and then displays an image through a monitor or a printout after performing appropriate imaging processing.

Digital radiography devices are used in dentistry to diagnose teeth and check whether prostheses have been correctly installed. Related thereto, a "Portable digital X-ray system" has been disclosed in Korean Patent Application Publication No. 10-2002-0008810. The system in the cited publication can be mounted with a vehicle, unlike a fixed type of the related art, but cannot be easily carried by a user.

Korean Patent Application Publication No. 10-2005-0090667 has proposed an apparatus of which the material and the mechanical configuration have been manufactured to be carried, but it does not consider the radiation time or the exposure dose of X-rays, so a patient is exposed to X-rays for too much time and it is inconvenient to use the apparatus due to heavy weight.

Korean Patent Application Publication No. 10-2008-0005000 has proposed a configuration that connects one or more diode in parallel to improve tube voltage and tube current ripples by improving a switching frequency and apply load corresponding to momentary load to a side of a diode where voltage is firstly applied in a multiplier circuit including a plurality of condenser and diodes connected to each other, in order to be applied to an X-ray generator of 100 kHz as a way of reducing an exposure dose.

However, arranging diodes in parallel to protect them from overcurrent is not actually needed because the current range used for X-rays is low and narrow. Further, a temporary peak voltage is generated at the output port of a high-voltage transformer and accordingly X-rays cannot be accurately controlled, so obtained images are dim or milky white and the lifespan of an apparatus may be reduced. Accordingly, it is required to maintain a predetermined voltage without overvoltage.

Further, increasing a switching voltage causes a problem with insulation, but the configurations described above do not consider this insulation problem, so complete insulation is strongly required.

Further, dental radiograph devices of the related art cannot be simply operated for patients, so it is required to further reduce the size and weight and ergonomically design the devices to conveniently use them for a longer period of time for patients.

Further, it has been reported that the more dental X-ray treatments a patient receives, the larger the danger of thyroid gland-related disease becomes, maximally by five times (by Dr. Anjum Memon, Brighton-sussex medical college, U.K), but X-ray generators using high frequencies use a switching frequency of 40 kHz or less in our country, so ripples are large and a rising time and a falling time are long, which increases an X-ray exposure dose, and accordingly, it is an urgent need to solve this problem. Further, since electronic parts are also reduced in lifespan when they are exposed to X-rays for a long period of time, it is difficult to use expensive equipment for a long period of time.

DISCLOSURE

Technical Problem

The present invention has been proposed to solve the problems in the related art. An object of the present invention is to minimize an X-ray exposure dose by reaching a predetermined voltage allowing for radiography in short time without delay due to a rising time, at a switching frequency of 100 kHz~10 tHz.

Another object of the present invention is to operate a radiograph device accurately and stably without error and increase the lifespan by preventing interference between coils through improvement of the structure of a bobbin for winding wires in a high-voltage transformer and by maintaining voltage and current applied to an X-ray tube accurately without error by suppressing current leakage.

Another object of the present invention is to improve convenience for a patient and ensure quality of an image by making and recording a lookup table in a memory for X-ray radiation times according to teeth or the types of treatment so that a user can select items through simple operation.

Another aspect of the present invention is to enable a small-sized battery to output a large amount of power ($10c$~$20c$) by improving the structure of the battery in order to minimize a radiation time by allowing a device to be stably operated at a switching frequency of 100 kHz~10 tHz.

TECHNICAL SOLUTION

In order to achieve the objects, the present invention provides a dental radiography device having a switching frequency of 100 kHz~10 tHz for a high-voltage transformer, tube voltage of 60 kV~70 kV, and tube current of 1 mA~2 mA.

The high-voltage transformer may include: a hollow bobbin having, around an outer side, a blocking wall separating a primary coil and a secondary coil and a plurality of separation walls for ensuring a plurality of spaces for winding the secondary coil, the blocking wall and the separation wall spaced from each other perpendicular to a shaft; the primary and the secondary coils wound around the bobbin; and primary coil and secondary coil connection terminals formed at the bobbin so that an input/output terminal of the primary coil and an input/output terminal of the secondary coil are separated, in which the primary coil and the secondary coil may not interfere with each other.

A high-voltage multiplying circuit at a side of the high-voltage transformer has an overvoltage protection circuit in which a plurality of pairs of diodes and condensers is connected in parallel and two or more diodes are connected in series to an end of the first diode at an end of the high-voltage multiplying circuit, that is, at an output side of the high-voltage transformer, so accurate tube voltage can be provided.

A plurality of holes, including holes for each condenser, is formed in a board where the high-voltage multiplying circuit and insulating oil is injected through the holes, so insulating effect is improved and a current leakage is prevented.

Further, X-ray radiation times are set within 0.01~0.2 seconds and recorded in a memory in accordance with teeth, and when a user selects a desired tooth to scan through a display unit and an input unit on a case, an exposure time is automatically adjusted in accordance with the selection.

A power supply formed by connecting a plurality of module type power supplies in series in which insulating papers are disposed at both sides of a thin film anode made of copper and a plurality of thin film power units formed by stacking thin film cathodes made of aluminum is stacked, so the power supply despite being in small in size can output a large amount of electricity over 100 number of times in a small size.

Advantageous Effects

According to the present invention, it is possible to reduce ripples using a high-frequency inverter having a switching frequency of 100 kHz or more and reduce a rising time and a falling time when radiating X-rays, so appropriate tube voltage is generated right after power is supplied. Accordingly, the exposure dose can be largely reduced and the exposure dose to a human body can be decreased, so deterioration in performance of the electronic device can be reduced.

Further, it is possible to protect a circuit from overvoltage suddenly generated by a high-voltage multiplying circuit and obtain accurate output voltage, so scanning can be accurately performed.

Further, by improving the structure of a high-voltage transformer, a primary coil and the secondary coil do not interfere with each other, so voltage from a power supply can be stably boosted and wiring is easy, and thus it can be commercially used.

Further, charging is required every time even though a frequency of 45 kHz is used in the related art, but the device of the present invention can be used hundreds of times even using 100 kHz, so the device can be used for two or more days in common dental clinics without charging.

Further, the focal spot of the device is small, so high-quality images can be obtained.

Further, by reducing the size of the arrangement structure of the high-voltage transformer and the high-voltage multiplying circuit and the power supply, the entire size of the device can be reduced, so it is possible to provide a device of about 1.7 kg or less, and accordingly, the device can be operated even by women without difficulty.

DESCRIPTION OF DRAWINGS

FIG. 1 is an exploded perspective view showing a dental radiograph device according to the present invention.

FIG. 2 is a cross-sectional view showing an X-ray tube.

FIG. 3 is a view showing a coil winding structure of a high-voltage transformer of the present invention.

FIG. 4 is a view showing the actual size of a high-voltage transformer of the present invention.

FIG. 5 is a view showing an example of arrangement of a high-voltage transformer and a multiplier circuit.

FIG. 6 is a view showing a configuration for preventing overvoltage in a high-voltage multiplier circuit.

FIGS. 7 and 8 are views showing the configuration of a power supply.

FIGS. 9 and 10 are views showing an electrical configuration of a radiography device of the present invention.

FIG. 11 is a view showing X-ray images by the present invention and the related art.

FIG. 12 is a view showing the size of a radiography device of the present invention.

MODE FOR INVENTION

Hereinafter, embodiments of the present invention will be described with reference to the accompanying drawings.

A dental radiography device according to the present invention includes a power supply outputting electricity of 10 c~20 c, a switching unit outputting a high-frequency signal by switching output values from overvoltage and overcurrent to 100 kHz~10 tHz, a high-voltage transformer amplifying a signal from the switching unit, and a high-voltage multiplier circuit converting output voltage from the high-voltage transformer into boosting voltage or DC voltage and including an overvoltage protection circuit.

Referring to FIG. 1, the radiography device largely includes a case 10 capable of being held by hand and having an X-ray radiation hole 12, an X-ray generator 20 disposed inside the case 10 and generating X-rays in response to a signal from the outside, an X-ray guide 30 guiding the X-rays from the X-ray generator 20 to the outside through the X-ray radiation hole 12, and a cap 40 covering an end of the X-ray guide 30.

In this configuration, there are provided various parts for gripping and operating the radiograph device in the case 10, including a display 13 for showing images, various control knobs N1~N3 for controlling operation to make the X-ray generator 20 generate X-rays, an input unit including a touch panel, and a handgrip 14 for holding the device with hands during scanning.

The X-ray generator 20 includes, as shown in FIGS. 1 and 2, a housing 21 that is made of aluminum, is plated with a material (for example, lead) that blocks X-rays and is easily soldered, on the inner side, and houses an X-ray tube for generating X-rays, a filament transformer for supplying power to a filament in the X-ray tube, a high-voltage multiplier circuit, and a high-voltage transformer, and is filled with insulating oil, an X-ray radiation tube 22 formed at a side of the housing 21 and preventing diffusion of X-rays, and a power supply 25 disposed on a side of the housing 21 to supply power to the housing 21.

The X-ray tube 12, as shown in FIG. 2, has a discharge hole 23b formed at a side of the aluminum tube 12a filled with insulating oil and blocked by transparent nylon resin (an acryl plate), a high-vacuum glass pipe 23c disposed in the aluminum tube 23a, and an electron generator 23d and an X-ray generating unit 23e disposed in the high-vacuum glass pipe 23c.

The electron generator 23d is electrically connected to a cathode (−) and has a focusing electrode 23d-1 having a tungsten filament therein. Electrons discharged from the tungsten filament in the focusing electrode 23d-1 are accelerated by high voltage applied to a cathode and an anode in high-vacuum pipe and hit against a target 23e-1 of the X-ray generating unit 23e facing the cathode.

The X-ray generating unit 23e includes a stator 23e-1 at the outside, a rotary 23e-3 at the inside, and the target 23e-1 connected to a side of the rotary 23e-3 through a shaft. The X-ray generating unit 23e is connected to the anode (+) and current flowing through a coil C wounding around the stator 23e-rotates the rotor 23e-3 by generating an electromagnetic force, so the target 23e-1 connected to a side of the rotor 23e-3 through a shaft is also rotated.

In the X-ray tube 23 having this configuration, when electrons discharged from the focusing electrode 23d-1 hit against the rotating target 23e-1, X-rays are generated, and some of the X-rays are discharged out of the tube through the discharge hole 23b whereas the other is blocked.

A process of setting coils in the high-voltage transformer T is described with reference to FIGS. 3 and 4. First, a primary coil 110 and a secondary coil 120 are wound around a bobbin B and completely separated by a blocking wall 130, with an input/output terminal 112 of the primary coil 110 and an input/output terminal 122 of the secondary coil 120 separated so that the primary coil 110 and the secondary coil 120 do not interfere with each other, thereby boosting voltage applied from the power supply.

The secondary coil 120 has a diameter of 0.08 mm~0.085 mm, but when the diameter is under 0.08 mm, desired output voltage cannot be obtained, and when the diameter is over 0.085 mm, the size of the high-voltage transformer increases. The secondary coils are sequentially wound in a plurality of spaces divided by the separation walls 124 in accordance with a predetermined number of windings and slits 126 for passing the secondary coils are formed in the separation walls 124 to connect the secondary coils 120 in the spaces.

A core is inserted into the bobbin B with the coils wound, an L value is measured with an LCR meter and whether the L value is within a predetermined range is checked, and the bobbin and the core are primarily fixed by taping and secondarily, the joint of two cores is bonded.

The high-voltage transformer of the present invention is small, 3 cm or less in size.

The high-voltage transformer T is disposed adjacent to the high-voltage multiplier circuit 200, as shown in FIG. 5, and a plurality of holes 220 is formed through a substrate 210 where the high-voltage transformer and the high-voltage multiplier circuit are disposed to pass the insulating oil, in which a hole 220 is formed in each condenser C.

On the high-voltage multiplier circuit 200, as shown in FIGS. 5 and 6, diodes D and D1 and condensers C are disposed in parallel at the output side of the high-voltage transformer T, and one or more diodes D2 for protection against overvoltage are connected in series to then ends of the diodes D1 at the end of the high-voltage multiplier circuit, that is, the output side of the high-voltage transformer so that the circuit can be protected from overvoltage and accurate tube voltage can be provided.

The power supply 25 is formed by connecting two or more module type power supplies 350 in series, as shown in FIGS. 7 and 8, in which insulation papers 320 are disposed at both sides of a thin film anode 310 made of copper and a plurality of thin power units 340 formed by stacking thin film cathodes 330 made of aluminum is stacked with an insulating paper (not shown) therebetween, so the power supply 25 can stably output a large amount of electricity (10c) over 100 number of times in a small size.

A focal spot of the radiography device means the focus size of a target, and the smaller the focal spot, the higher the quality of an image that can be obtained. Domestic products have a 0.8 mm focal spot and the present invention provides a high-quality image using a focal spot of 0.4 mm.

The electrical configuration of the radiography device of the present invention having this configuration is described with reference to FIGS. 9 and 10.

As shown in FIG. 9, the dental radiography device according to the present invention largely includes: a tube voltage generator 410 generating necessary tube voltage (60 kV~70 kV); a tube current generator 420 generating tube current (1 mA~2 mA), a switching unit 430 transmitting the tube voltage and the tube current to a high-voltage transformer T and filament transformer T1 in accordance with a predetermined switching frequency; a high-voltage multiplier circuit 200 multiplying the high-voltage transformer T and the filament transformer T1, which are connected to the rear end of the switching unit 430 and transmit voltage to the X-ray tube 440, by a predetermined value and transmitting the voltage to the X-ray tube 440; a detecting/checking unit 450 detects an error by detecting tube voltage, tube current, and temperature of the radiography device and outputs a result based on the error; an input unit 460 for selecting various operations of the radiography device; a display unit 13 displaying various operation states; and a control unit 470 controlling the components in the radiograph device in response to signals from the input unit 460 and the detecting/checking unit 450.

The tube current generator 420 includes a pulse width modulator (PWM) circuit and an oscillator and sets tube current a predetermined value inputted within a predetermined range (1~3 mA) by adjusting output from the pulse width modulator (PWM) within a predetermined range.

Further, the tube voltage generator 410 also includes a pulse width modulator (PWM) and an oscillator, makes PWM output within 100 kHz~10 tHz, and sets tube voltage to a predetermined level within a predetermined range (60~70 kV).

The detecting/checking unit 450 detects tube voltage and tube current, compares their maximum and minimum values (MAX & MIN) and transmits the result to the control unit 470, and determines whether the internal temperature of the housing 21 is within a predetermined range (50☐~55☐) and transmits the result to the control unit 470, and detects and checks various operation states and transmits the results to the control unit.

The high-voltage transformer T is operated at a predetermined switching frequency (100 kHz~10 tHz) and applies boosted output voltage to the high-voltage multiplying circuit 200.

The high-voltage multiplying circuit 200 (positive & negative operation) is composed of a plurality of diodes (high-voltage diode: 12 kV or more) and capacitors (high-voltage capacitor: 15 kV or more) and disposed in parallel at the output terminal of the high-voltage transformer, converts output from the high-voltage transformer into boosting voltage and DC voltage in each step in accordance with positive/negative operation, and produces and supplies output voltage to the X-ray tube by operating by two times, eight times, or sixteen times.

When the radiography device of the present invention was operated at a switching frequency of 120 kHz, as shown in FIG. 11, an excellent image could be obtained, the time taken to obtain the image was 0.01~0.2 seconds, which is much shorter than 0.35~0.7 seconds when the switching frequency was 40 kHz in the related art, and a clear image could be obtained.

When the scanning time is less than 0.01 seconds, the predetermined voltage for operating the device cannot be reached and image cannot be obtained, and when it exceeds 0.2 seconds, unnecessary exposure is made and there is no reason to continue the operation.

Further, since scanning was possible within a short time, an exposure dose per hour at 120 kHz was 1.2 μSV, which was largely reduced as compared with the exposure dose per hour of 0.03 mSV at 45 kHz in the related art and which is a little higher than the exposure dose of 0.14 μSV generated in the nature.

The dental radiography can scan all teeth within 0.01~0.2 seconds, so radiation times are set within 0.01~0.2 seconds and recorded in a memory, depending on teeth (teeth of a child and an adult, and a cheek tooth, and a canine tooth). Further, when a user selects a desired tooth to scan through the display unit and the output unit on the case, the exposure time is automatically adjusted in accordance with the selection.

Since the radiography device of the present invention has a high switching frequency, the size of the high-voltage transformer reduces and the battery structure is improved. Accordingly, as shown in FIG. 12, the entire size of the radiography device is largely decreased and the weigh is small, about 1.7 kg, as compared with radiography devices of the related art, so the radiography device can be operated even by women without difficulty.

The invention claimed is:

1. A dental radiograph device comprising:
    an X-ray tube including a filament and generating X-rays;
    a high-voltage transformer operating at a switching frequency of 100 kHz~10 tHz, amplifying input signals by using a power supply that outputs electricity of 10 c~20 c, and wound with a primary coil and a secondary coil without interference with each other, the secondary coil having a diameter of 0.08 mm~0.085 mm, so as to minimize an X-ray exposure dose by reaching a predetermined voltage allowing for radiography in short time without delay through reducing a rising time and a falling time when radiating X-rays, at the switching frequency of 100 kHz~10 tHz;
    a filament transformer supplying power to the filament in the X-ray tube;
    a high-voltage multiplying circuit including an overvoltage protection circuit and converting output voltage from the high-voltage transformer into boosting voltage or DC voltage; and
    a power supply formed by connecting a plurality of module type power supplies in series in which insulating papers are disposed at both sides of a thin film anode made of copper and a plurality of thin film power units formed by stacking thin film cathodes made of aluminum is stacked and having output of 10 c~20 c,
    wherein 0.01~0.2 seconds are taken to scan a tooth.

2. The dental radiograph device of claim 1, wherein the high-voltage transformer includes:
    a hollow bobbin having, around an outer side, a blocking wall separating a primary coil and a secondary coil and a plurality of separation walls for ensuring a plurality of spaces for winding the secondary coil, the blocking wall and the separation wall spaced from each other perpendicular to a shaft;
    the primary and the secondary coils wound around the bobbin; and
    primary coil and secondary coil connection terminals formed at the bobbin so that an input/output terminal of the primary coil and an input/output terminal of the secondary coil are separated,
    wherein the primary coil and the secondary coil do not interfere with each other.

3. The dental radiography device of claim 1, wherein the high-voltage multiplying current has an overvoltage protection circuit in which diodes and condensers are arranged in parallel at an output side of the high-voltage transformer and two or more diodes for protection from overvoltage are connected in series to ends of the diodes at the output side of the high-voltage transformer that is an end of the high-voltage multiplying circuit.

4. The dental radiography device of claim 2, wherein a board where the high-voltage transformer and the high-voltage multiplying circuit are disposed adjacent to each other has a plurality of holes including holes formed at positions corresponding to condenser so that insulating oil is injected through the holes.

5. The dental radiography device of claim 3, wherein a board where the high-voltage transformer and the high-voltage multiplying circuit are disposed adjacent to each other has a plurality of holes including holes formed at positions corresponding to condenser so that insulating oil is injected through the holes.

6. The dental radiography device of claim 1, wherein X-ray radiation times are set within 0.01~0.2 seconds and recorded in a memory in accordance with teeth, and when a user selects a desired tooth to scan through a display unit and an input unit on a case, an X-ray radiation time is set in accordance with the selection.

7. The dental radiography device of claim 1, wherein the X-ray tube is 10 mm~56 mm long and has a focal spot of 0.01 μm~0.4 mm.

* * * * *